United States Patent
Foldvari et al.

[11] Patent Number: 5,993,852
[45] Date of Patent: *Nov. 30, 1999

[54] BIPHASIC LIPID VESICLE COMPOSITION FOR TRANSDERMAL ADMINISTRATION OF AN IMMUNOGEN

[75] Inventors: Marianna Foldvari; Maria Baca-Estrada, both of Saskatchewan, Canada

[73] Assignee: PharmaDerm Laboratories LTD., Saskatchewan, Canada

[*] Notice: This patent is subject to a terminal disclaimer.

[21] Appl. No.: 09/141,875

[22] Filed: Aug. 27, 1998

Related U.S. Application Data

[60] Provisional application No. 60/057,597, Aug. 29, 1997.
[51] Int. Cl.$^6$ ............ A61K 9/127; A61K 39/00; A61K 9/70
[52] U.S. Cl. ............ 424/450; 424/449; 424/93.1; 424/193.1; 424/196.11; 424/234.1; 424/812; 436/829; 264/41; 264/43
[58] Field of Search ............ 424/450, 193.1, 424/196.11, 234.1, 93.1, 812, 449; 436/829; 264/4.1, 43

[56] References Cited

U.S. PATENT DOCUMENTS

| | | |
|---|---|---|
| 4,053,585 | 10/1977 | Allison et al. . |
| 4,911,928 | 3/1990 | Wallach ........................... 424/450 |
| 4,921,757 | 5/1990 | Wheatley ........................ 428/402.2 |
| 5,100,662 | 3/1992 | Bolcsak et al. . |
| 5,340,588 | 8/1994 | Domb . |
| 5,464,630 | 11/1995 | Six et al. . |
| 5,643,577 | 7/1997 | Pang et al. . |
| 5,718,914 | 2/1998 | Foldvari . |

FOREIGN PATENT DOCUMENTS

| | | |
|---|---|---|
| 95/03787 | 2/1995 | WIPO . |
| 97/20576 | 6/1997 | WIPO . |

Primary Examiner—Gollamudi S. Kishore
Attorney, Agent, or Firm—Judy M. Mohr; Dehlinger & Associates

[57] ABSTRACT

A composition for transdermal administration of an immunogen is described. The immunogen is entrapped in lipid vesicles having a oil-in-water emulsion in the central core compartment. The vesicles are administered transdermally to elicit an immune response in a subject.

28 Claims, 6 Drawing Sheets

BIPHASIC LIPID VESICLE COMPOSITION FOR TRANSDERMAL ADMINISTRATION OF AN IMMUNOGEN

This application claims the priority of U.S. provisional application Serial No. 60/057,597, filed Aug. 29, 1997, which is incorporated herein by reference.

FIELD OF THE INVENTION

The present invention relates to administration of an immunogen for purposes of immunization or vaccination. The immunogen is entrapped in lipid vesicles having an oil-in-water emulsion in the central core compartment. The vesicles are administered transdermally for administration of the entrapped immunogen.

REFERENCES

Benson, M. L., et al., Can. J. Comp. Med.* 42:368–369 (1978).

Berggren, K. A., et al., Am. J. Vet. Res. 42:1383–1388 (1981).

Chanock, R. M., Lerner, R. A., Brown, F. and Ginsberg, H, "New Approaches to Immunization, Vaccines" 86, Cold Spring Harbor, N.Y. (1987).

Collier, J. R., et al., *Am. J. Vet. Med. Assoc.* 140:807–810 (1962).

Czerkinsky, C., et al., *J. Immunol. Methods* 110:29–36 (1988).

Harland, R. J., et al., *Can. Vet. J.* 33:734–741 (1992).

Santus, G. C. and R. W. Baker, *J. Controlled Release,* 25:1–20 (1993).

BACKGROUND OF THE INVENTION

An immune response can be induced against an almost limitless variety of substances. There are two categories of immune response, humoral and cellular. In a humoral response, the antigen or foreign substance is recognized by specific receptors on the surfaces of lymphocytes and certain B-lymphocytes are stimulated to multiply. These cells produce vast numbers of antibodies capable of binding to the antigens. After binding, the bound antigen is removed or destroyed. In a cellular or cell-mediated immune response, T-lymphocytes, in particular helper and killer T-lymphocytes, are active in recognizing and destroying the foreign substance.

The process of inducing immunity as a preventive measure against infectious diseases is referred to as immunization. Immunization can be passive, where antibodies are administered to an animal to provide a short-term immunity, or active. Active immunization is more commonly known as vaccination, where a killed or weakened antigen, or fragment thereof, is introduced to an animal. The antigens sensitize the immune system so that if that antigen later enters the body, antibodies are quickly produced to remove and/or destroy the invading antigen.

Most vaccines are preparations containing the organism, or parts of organism, against which protection is sought. The organism is killed or weakened sufficiently so as not to cause disease but to induce immunity. Some vaccines contain chemically modified bacterial toxins. Vaccines against a variety of infectious diseases are available, for example, live attenuated vaccines are given to protect against measles, mumps, rubella, yellow fever and polio. Diphtheria and tetanus vaccines contain inactivated bacterial toxins.

Cholera, typhoid fever, pertussis, rabies, viral hepatitis B and influenza contain killed organisms, or in the case of hepatitis B, only a part of the virus.

Vaccines are usually given by injection into the upper arm, or in the case of polio vaccine, administered orally. Administration via injection is not always convenient, particularly in third world countries, for soldiers in the field or for subjects other than humans, including horses, cows and dogs.

SUMMARY OF THE INVENTION

Accordingly, it is an object of the invention to provide an easy, effective mode of administering a vaccine.

It is a further object of the invention to provide a biphasic lipid vesicle composition for transdermal administration of an antigen entrapped in the lipid vesicles.

In one aspect, the invention includes a composition for eliciting in a subject an immune response to an immunogen. The composition includes a suspension of biphasic lipid vesicles having a central core compartment containing an oil-in-water emulsion, and, entrapped in the biphasic lipid vesicles, an immunogen.

In one embodiment, the immunogen is an antigen derived from bacterial, viral, parasitic, plant or fungal origin.

The immunogen is effective to elicit a humoral immune response, or alternatively, is effective to elicit a cell-mediated immune response.

The composition in another embodiment, further includes an adjuvent entrapped in the lipid vesicles.

In another embodiment, the suspension of lipid vesicles further includes a skin permeation enhancer.

Preferred permeation enhancers include fatty acylated amino acids and unsaturated fatty acids.

In another aspect, the invention includes a method for eliciting in a subject an immune response to an immunogen. The method includes administering transdermally to the subject, a dose of the immunogen. As described above, the immunogen is entrapped in biphasic lipid vesicles having a central core compartment containing an oil-in-water emulsion.

In still another aspect, the invention includes a method for transdermally administering an immunogen to a subject by applying a device to the skin of a subject. The device includes (i) a suspension of lipid vesicles formed by mixing an oil-in-water emulsion with vesicle-forming lipids. The vesicles are composed of (a) a lipid-bilayer outer membrane composed of such vesicle-forming lipids, (b) a central core compartment containing such an oil-in-water emulsion and (c) entrapped in the vesicles, a dose of an immunogen effective to elicit an immune response; (ii) a reservoir adapted to retain the lipid vesicle suspension and adapted for release of lipid vesicles therefrom; and (iii) means for affixing the device to a subject for transdermal administration of the immunogen.

In still another aspect, the invention includes a device for transdermal administration of an immunogen including a suspension of lipid vesicles formed by mixing an oil-in-water emulsion with vesicle-forming lipids. The vesicles are composed of (i) a lipid-bilayer outer membrane composed of such vesicle-forming lipids, (ii) a central core compartment containing such an oil-in-water emulsion and (iii) entrapped in the vesicles, a dose of an immunogen effective to elicit an immune response. The device also includes a reservoir adapted to retain the lipid vesicle suspension and adapted for release of lipid vesicles therefrom and means for affixing the device to a subject for transdermal administration of the immunogen.

In one embodiment, the reservoir in the device is defined by an impermeable backing member and a membrane effective in use to allow passage of lipid vesicles from the reservoir.

In another embodiment, the suspension of lipid vesicles includes a permeation enhancer. For example, the permeation can be a fatty acylated amino acid or an unsaturated fatty acid.

The immunogen entrapped in the vesicles preferably has a molecular weight of between about 100–100,000,000 daltons. In one embodiment, the immunogen is one for use in vaccinating an animal or a human.

Means for affixing the device to the subject is, in one embodiment, an adhesive layer adjacent the membrane.

The suspension of vesicles can include an adjuvant, entrapped in the lipid vesicles or included in the suspension.

These and other objects and features of the invention will be more fully appreciated when the following detailed description of the invention is read in conjunction with the accompanying drawings.

DETAILED DESCRIPTION OF THE INVENTION

I. Definitions

The following terms as used herein shall have the following meanings.

"Antigen" refers to a substance or material that is recognized specifically by an antibody and/or combines with an antibody.

"Adjuvant" refers to a substance or material that potentiates an immune response when administered in conjunction with an antigen. An adjuvant can also be used to elicit an immune response more rapidly.

"Biphasic lipid vesicles" refer to lipid particles formed of a vesicle-forming lipid and having an oil-in-water emulsion in the central core compartment. The terms lipid vesicle, vesicle, and biphasic lipid vesicle are used herein interchangeably.

"Immunogen" refers to a substance or material, including an antigen, that is capable of inducing an immune response. Immunogens can elicit immune responses either alone or in combination with an adjuvant. An immunogen can be synthetic or natural and can be, for example, an inorganic or organic compound such as a hapten, a protein, peptide, polysaccharide, nucleoprotein, nucleic acid or lipoprotein. Immunogens may be derived from a bacterial, viral or protozoal, plant, or fungal organism or fractions thereof.

"Dose" refers to the amount of immunogen needed to elicit an immune response. The amount varies with the animal, the immunogen and the presence of adjuvant as described hereinbelow. The immunization dose is readily determined by methods known to those of skill in the art, such as through host animal immunization and challenge studies (Chanock, et al., (1987)).

"Reservoir" refers to a storage structure that can retain and distribute therein a medium.

II. Biphasic Lipid Vesicle Suspension

A. Biphasic Lipid Vesicles

Figure 1:
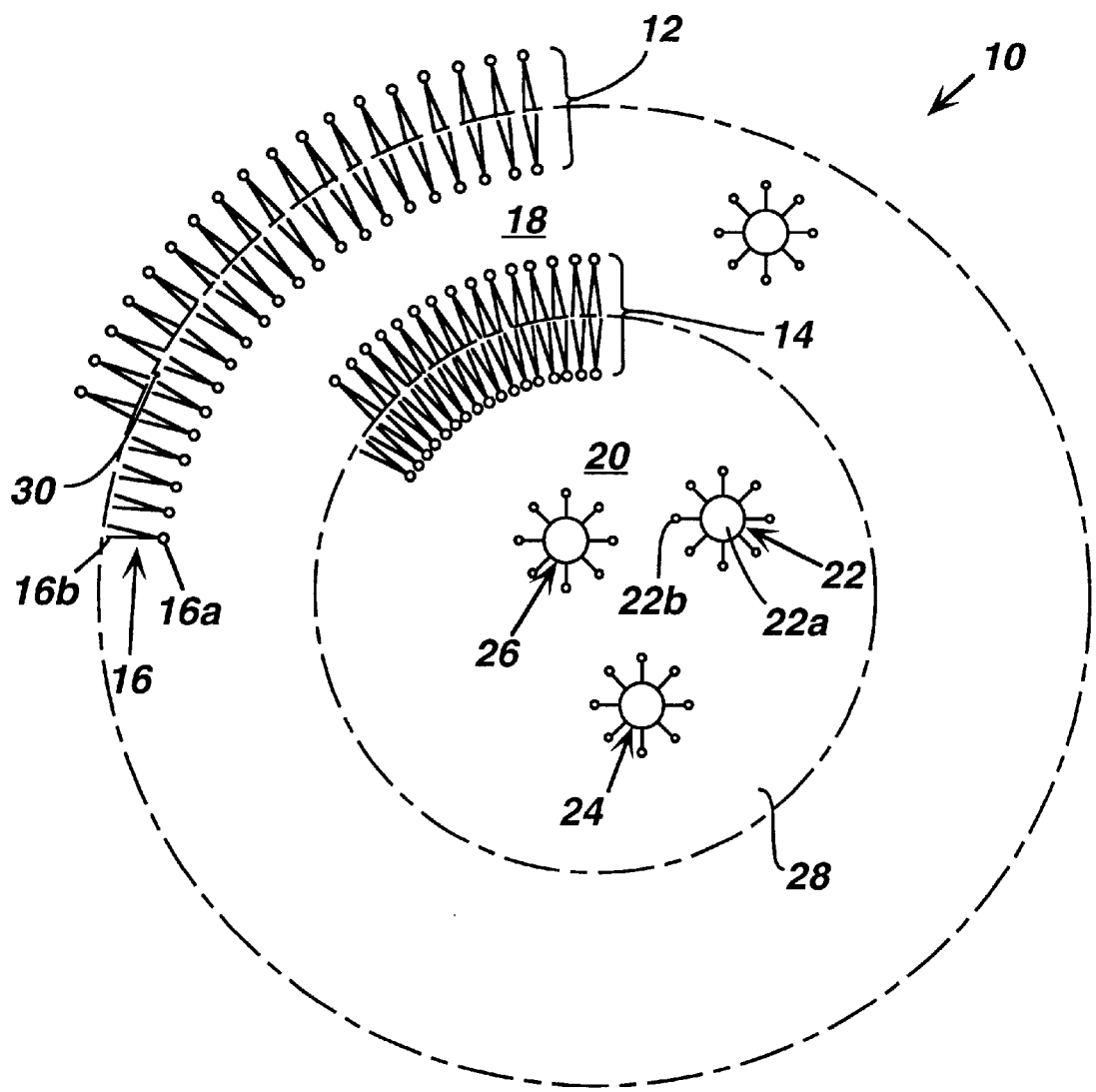
FIG. 1 illustrates a biphasic lipid vesicle prepared in accordance with the invention.

As discussed above, the invention includes a composition of lipid vesicles for transdermal administration of an immunogen. A lipid vesicle in accordance with the invention is illustrated schematically in FIG. 1.

Referring now to this figure, the biphasic lipid vesicles of the present invention are multilamellar lipid vesicles, like vesicle 10 shown in the figure, composed of a series of lipid bilayers, two of which are shown in part as bilayers 12, 14. Each lipid bilayer is composed of two layers of a vesicle-forming lipid, discussed below, where each lipid molecule, such as molecule 16, is oriented with its polar head group 16a exposed to a hydrophilic compartment 18 and its hydrophobic tail 16b aligned with neighboring lipid molecules.

The innermost bilayer in the vesicle defines a central core compartment 20. According to an important feature of the invention, the core compartment of the lipid vesicle contains an oil-in-water emulsion, represented in the figure by droplets 22, 24, 26. As will be discussed below, the oil-in-water emulsion is entrapped in the lipid vesicles by preparing a surfactant-stabilized oil-in-water emulsion, represented in the figure as lipophilic droplet 22a surrounded by a layer of surfactant molecules 22b. The emulsion is mixed with vesicle-forming lipids to form lipid bilayers around the emulsion.

The immunogen can be entrapped in the lipid vesicles in a variety of places, depending on physicochemical properties of the immunogen. For example, a hydrophilic immunogen can be the water phase of the oil-in-water emulsion in the central core compartment or in the water phase in compartment 18 between the lipid bilayers. A more hydrophobic immunogen can be contained in the oil phase of the oil-in-water emulsion or in the lipid bilayer, as indicated at 30 in the figure. Methods of preparing the biphasic lipid vesicles for entrapment of the immunogen are described below.

B. Biphasic Lipid Vesicle-Entrapped Immunogen

As discussed above, the composition of the present invention includes a suspension of biphasic lipid vesicles containing an entrapped immunogen effective to elicit an immune response, e.g., for purposes of immunization or vaccination.

In general, a wide variety of immunogens are suitable for use in the present invention. The following list of antigens is provided by means of illustration and is not meant to be exclusive: influenza virus antigens (such as haemagglutinin and neuraminidase antigens), *Bordetella pertussis* antigens (such as pertussis toxin, filamentous haemagglutinin, pertactin), human papilloma virus (HPV) antigens, *Helicobacter pylori* antigens, rabies antigens, tick-borne encephalitis (TBE) antigens, meningoccal antigens (such as capsular polysaccharides of serogroup A, B, C, Y and W-135), tetanus antigens (such as tetanus toxoid), diphtheria antigens (such as diphtheria toxoid), pneumococcal antigens (such as *Streptococcus pneumoniae* type 3 capsular polysaccharide), tuberculosis antigens, human immunodeficiency virus (HIV) antigens (such as GP-120, GP-160), cholera antigens (such as cholera toxin B subunit), staphylococcal antigen (such as staphylococcal enterotoxin B), shigella antigens (such as shigella polysaccharides), vesicular stomatitis virus antigen (such as vesicular stomatitis virus glycoprotein), cytomegalovirus (CMV) antigens, hepatitis antigens (such as hepatitis A (HAV), B (HBV), C (HCV), D (HDV) and G (HGV) virus antigens, respiratory syncytial virus (RSV) antigens, herpes simplex antigens, or combinations thereof (e.g., combinations of diphtheria, pertussis and tetanus (DPT)). Suitable antigens also include those delivered for induction of tolerance, such as retinal antigens. Antigens for immunization/vaccination against anthrax and *Yersinia pestis* are also contemplated.

Preferred antigens include *Bordetella pertussis* antigens, meningococcal antigens, tetanus antigens, diphtheria antigens, pneumococcal antigens, tuberculosis antigens and RSV antigens. In another preferred embodiment, the entrapped immunogen has a molecular weight of between about 100–100,000,000 daltons, more preferably 100–500,000 daltons, and most preferably 100–100,000 daltons.

In studies performed in support of the present invention, leukotoxin, an exotoxin produced by *Pasteurella haemolytica,* and hen egg lysozyme were entrapped in biphasic lipid vesicles and delivered transdermally, as will be described below.

III. Preparation of Biphasic Lipid Vesicles

As discussed above, the biphasic lipid vesicles of the present invention include in the central core compartment of the lipid vesicle, and in the aqueous space separating the lipid bilayers, an oil-in-water emulsion. In general, such lipid vesicles are prepared by mixing an oil-in-water emulsion with vesicle-forming lipids. Importantly, the oil-in-water emulsion is stabilized with a surfactant prior to mixing with the vesicle-forming lipids. That is, the oil droplets in the emulsion are surrounded by a surfactant, preferably, surrounded by a monolayer of surfactant. In a preferred embodiment, the stabilizing surfactant is other than the vesicle-forming lipid component forming the biphasic lipid vesicle bilayers.

Figure 2:
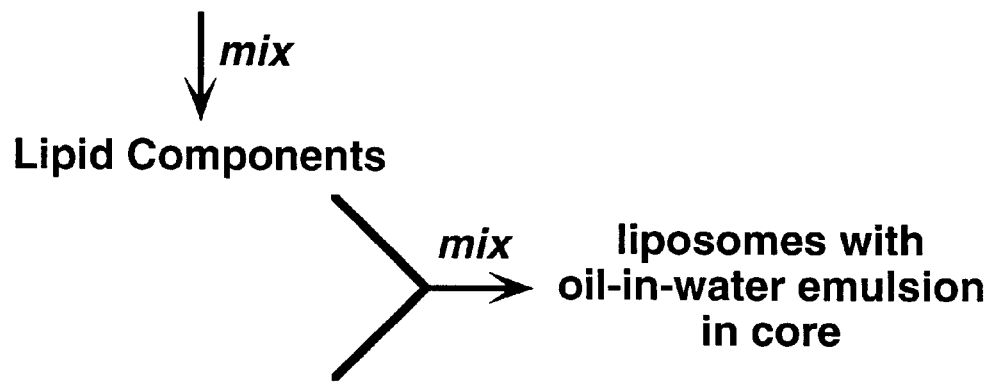
FIG. 2 shows a general scheme for preparing biphasic lipid vesicles having an oil-in-water emulsion in the central core, for use in the device of the invention.

More specifically, biphasic lipid vesicles in accordance with the present invention are prepared according to the general procedure outlined in FIG. 2. The selected lipid components are solubilized in a suitable solvent, which in a preferred embodiment, is a pharmaceutically acceptable hydrophilic solvent, such as a polyol, e.g., propylene glycol, ethylene glycol, glycerol, or an alcohol, such as ethanol, or mixtures of such solvents. Depending on the physicochemical properties of the lipid components and on the selected solvent, it may be necessary to warm the mixture, for example, to between 40–80 ° C.

The lipid components necessarily include a vesicle-forming lipid, by which is meant an amphipathic lipid having a hydrophobic tail and a head group which can form spontaneously into bilayer vesicles in water. The vesicle-forming lipids are preferably ones having two hydrocarbon chains, typically acyl chains, and where the head group is either polar or nonpolar. There are a variety of synthetic vesicle-forming lipids and naturally-occurring vesicle-forming lipids suitable for use, such as phospholipids, which include phosphatidylcholine, phosphatidylethanolamine, phosphatidylserine, phosphatidylinositol, phosphatidic acid, and sphingomyelin, where the two hydrocarbon chains are typically between about 14–22 carbon atoms in length, and have varying degrees of unsaturation. These lipids can be obtained commercially or prepared according to published methods.

In addition to the vesicle-forming lipid component, the lipid vesicles of the present invention can include other lipid components capable of being stably incorporated into lipid bilayers, with their hydrophobic moieties in contact with the interior, hydrophobic region of the bilayer membrane, and their polar head groups oriented toward the exterior, polar surface of the membrane. For example, glycolipids, ceramides and sterols, such as cholesterol, coprostanol, cholestanol and cholestane, long chain fatty acids ($C_{16}$ to $C_{22}$), such as stearic acid, can be incorporated into the lipid bilayer. Other lipid components that may be used include fatty amines, fatty acylated proteins, fatty acylated peptides, oils, fatty alcohols, glyceride esters, petrolatum and waxes. It will also be appreciated that a skin permeation enhancer can be included in the lipid vesicle lipid components, as will be further discussed below.

With continuing reference to FIG. 2, the oil-in-water emulsion is prepared by dissolving a surfactant in water or in oil, depending on the hydrophilic-lipophilic balance (HLB) of the surfactant. In a preferred embodiment, the surfactant is mixed with distilled water and added to an oil phase for formation of an emulsion. The emulsion can be formed using agitation such as homogenization or emulsification, or can be formed by micro-emulsion techniques which do not involve agitation. The resulting emulsion preferably has water as the continuous phase and oil as the dispersed phase.

According to an important feature of the invention, the oil-in-water emulsion is stable by virtue of the oil droplets in the dispersed phase being surrounded by the surfactant. That is, the hydrophilic portion of each surfactant molecule extends into the aqueous phase of the emulsion and the hydrophobic portion is in contact with the lipophilic droplet. As will be discussed below, lipid vesicles are formed by blending the oil-in-water emulsion with vesicle-forming lipids. If the emulsion is not surfactant-stabilized prior to contact with the vesicle-forming lipids, the vesicle-forming lipids may act to first stabilize the emulsion rather than form lipid bilayers around the oil-in-water emulsion.

Surfactants suitable for formation of the oil-in-water emulsion are numerous, including both cationic, anionic and nonionic or amphoteric surfactants. In one embodiment, the preferred surfactant is a cationic surfactant, such as linoleamidopropyl propylene glycol-dimonium chloride phosphate, cocamidopropyl propylene glycol-dimonium chloride phosphate and stearamido propylene glycol-dimonium chloride phosphate. These are synthetic phospholipid complexes commercially available from Mona Industries, Inc (Patterson, N.J.) sold under the tradenames Phospholipid EFA™ Phospholipid SV™ and Phospholipid SVC™, respectively. Another preferred vesicle-forming lipid for use as the primary lipid component of the biphasic lipid vesicle bilayers is hydrogenated phosphatidylcholine.

Exemplary anionic surfactants include acylglutamates, such as triethanolamine-cocoyl glutamate, sodium lauroyl glutamate, sodium hydrogenated tallow glutamate and sodium cocoyl glutamate.

Exemplary nonionic surfactants include naturally derived emulsifiers, such as polyethyleneglycol-60 almond glycerides, avocado oil diethanolamine, ethoxylated jojoba oil (polyethyleneglycol-40 jojoba acid and polyethyleneglycol-40 jojoba alcohol); polyoxyethylene derivatives, such as polyoxyethylene-20 sorbitan monooleate and polyoxythethylene-20 sorbitan monostearate; lanolin derivatives, such as polychol 20 (LANETH 20) and polychol 40 (LANETH 40); and neutral phosphate esters, such as polypropyleneglycol-cetyl ether phosphate and diethanolamine oleth-3 phosphate.

The oil droplets in the dispersed oil phase preferably have sizes of less than about 1 μm, more preferably less than about 0.5 μm, in diameter. The droplet size, of course, is readily adjusted by mixing conditions, e.g., shear and time of mixing, etc.

It will be appreciated that other components can be added to the oil-in-water emulsion, that is, the oil-in-water emulsion need not be of oil, surfactant and water alone. For example, the emulsion can include antimicrobial agents, such as methylparaben, propylparaben, and enhancing ingredients such as waxes, fatty alcohols, fatty acid esters, glyceryl stearate, petrolatum, plant oils and extracts, and combinations thereof. Specific preferred examples include beeswax, olive oil, glyceryl stearate, cetyl alcohol, stearyl alcohol, myristyl myristate, and cetyl palmitate, stearyl heptanoate, and stearyl palmitate. Exemplary formulations suitable for use in the present invention are described below and disclosed in co-owned U.S. application Ser. No. 08/507,923, which is incorporated by reference herein.

With continuing reference to FIG. 2, the stabilized oil-in-water emulsion is mixed with the solubilized vesicle-forming lipid and, if added, other lipid components, e.g., cholesterol. The emulsion and the lipid components are mixed under conditions effective to form multilamellar vesicles having in the central compartment the oil-in-water emulsion.

The size of the vesicles is typically between about 0.1–100 μm. For use in the present invention, a lipid vesicle size of between about 0.5–25 μm is preferred, which can be most readily obtained by adjusting the mixing conditions.

The composition of lipid vesicles formed in accordance with the invention have a consistency similar to a cream without further addition of thickening or gelling agents, and, therefore, are readily applied directly to the skin of a subject for transdermal administration of the entrapped immunogen. Alternatively, the lipid vesicle composition can be readily incorporated into the reservoir of a transdermal device.

The preparation procedure outlined in FIG. 2 results in a population of vesicles with a uniform size distribution and homogeneous composition, as has been discussed and shown in U.S. Pat. No. 5,853,755, which is expressly incorporated by reference herein in its entirety. The vesicles are physically stable, that is, little aggregation or fusion of vesicles is evident after storage for a four year period.

A. Other Lipid Vesicle Components

The immunogen, depending on its physicochemical properties, can be entrapped in the central core compartment of the vesicles, between the lipid bilayers, in the interior of the lipid bilayers as will be described.

Water soluble immunogens are entrapped in the central core compartment and in the peripheral compartments between the lipid bilayers by adding the immunogen to the water phase during preparation of the oil-in-water emulsion. The immunogen, dissolved or suspended in the water phase, is entrapped as part of the emulsion during lipid vesicle formation upon addition of the vesicle-forming lipids.

Lipophilic immunogens are added to the oil phase during preparation of the oil-in-water emulsion for entrapment in the central compartment and the peripheral compartments. Additionally or alternatively, lipophilic immunogens can be entrapped in the lipid bilayer by adding the immunogen to the vesicle forming lipid and/or the other lipid components, such as cholesterol.

In one embodiment of the invention, the biphasic lipid vesicles include a permeation enhancer to enhance the penetration of the entrapped antigen. The use of such enhancers has been widely studied in the transdermal art (Santus, et al., 1993) and it will be appreciated that such enhancers are suitable for use in the present invention. In preferred embodiments, the permeation enhancer is a fatty acylated amino acid, such as monolauroyllysine or dipalmitoyllysine, an unsaturated fatty acid, such as oleic acid, a short chain fatty acid, such as lauric acid or methyl salicylate. The penetration enhancer can be included in the oil-in-water emulsion or in the lipid bilayer, in the same manner as described above for including the entrapped immunogen.

In some embodiments, and as discussed above, the biphasic lipid vesicles prepared for use in the invention, include an antimicrobial agent, such as methyl paraben or propylparaben. Such agents can be added to the water phase when preparing the oil-in-water emulsion, and entrapped in the lipid vesicles as part of the water phase.

In another embodiment of the invention, an adjuvant is included in the biphasic lipid vesicle composition. Exemplary adjuvants include Complete Freund's Adjuvant (CFA), Incomplete Freund's Adjuvant (IFA), aluminum hydroxide, bacterial, viral or synthetic adjuvants. Adjuvants act by facilitating and slowing the release of immunogens at the point of administration. Oil-based adjuvants, for example, induce the formation of granulomas which are populated primarily by macrophages and other antigen presenting cells. Adjuvants also aid in the delivery of immunogens to the lymphatic system, placing the immunogens in close proximity to antigen presenting and immune effector cells.

While CFA is known to be a powerful adjuvant activator, its use is restricted to animal use due to the presence of heat killed Mycobaterium, or like antigenic epitopes. Alternatively, other adjuvant activators may be used such as heat killed members of the Corynebacterium or Bordatella species, bacterial cell peptidogycan or muramyl dipeptide, which localize antigens in T-cell dependent areas for antigen presentation and immune cell activation.

Another class of adjuvant activators for use with the present invention include amphipathic and surface active agents, such as saponin, lysolethicin, retinal, Quil A and pluronic polymer formulations. The efficacy of surface-active adjuvants is particularly noticeable when membrane components are used as immunogens. Other types of adjuvants include inert carriers such as bentonite and acrylic carriers; polyclonal T-cell activators such as purified protein derivative (PPD) and polyU:polyA.

IV. Transdermal Device

As discussed above, the biphasic lipid vesicle composition of the invention is for use in transdermal administration. The composition can be applied directly to the skin, e.g. applied as a lotion, cream or gel, or can be incorporated into a transdermal device. Such a device will now be described.

The transdermal device of the present invention includes, in its most basic embodiment, a reservoir adapted to retain during storage and release in operation lipid vesicles containing an entrapped immunogen. Exemplary devices are shown in FIGS. 3A–3C, however, it will be appreciated that a wide variety of transdermal devices have been described in the art and are suitable for use in the present invention.

Figure 3A:
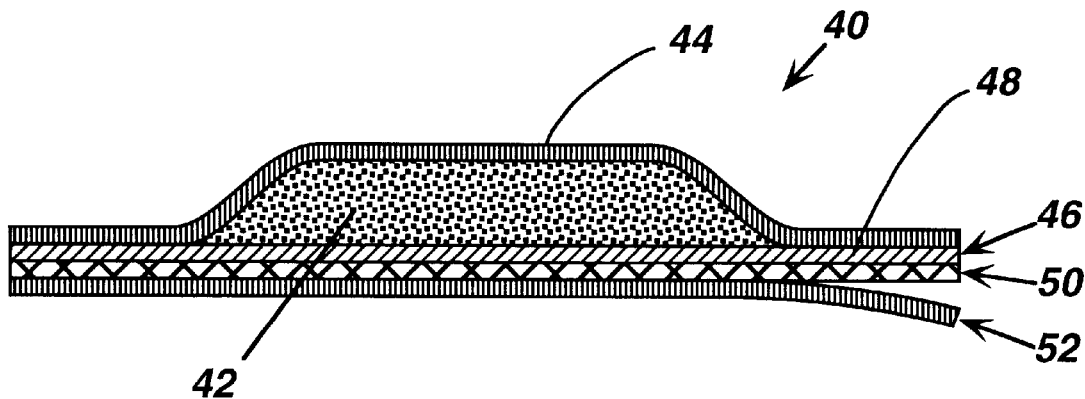
FIGS. 3A–3C are cross-sectional views of transdermal devices suitable for use in the present invention.
Figure 3B:
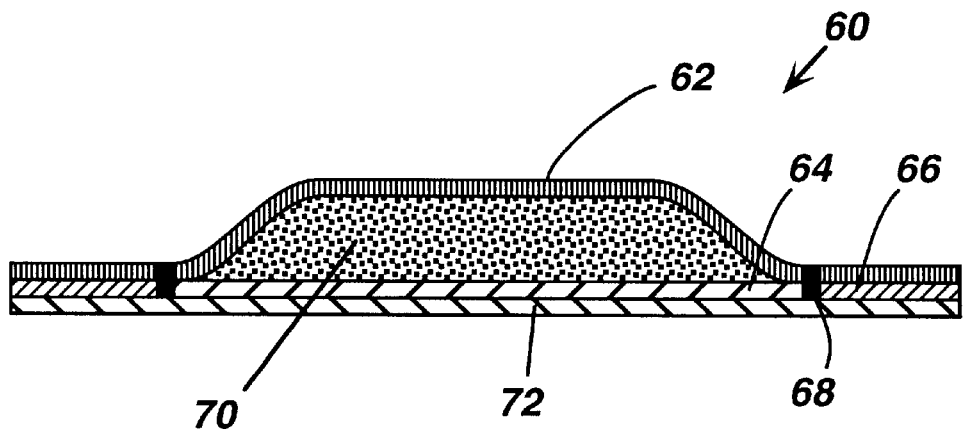
Figure 3C:
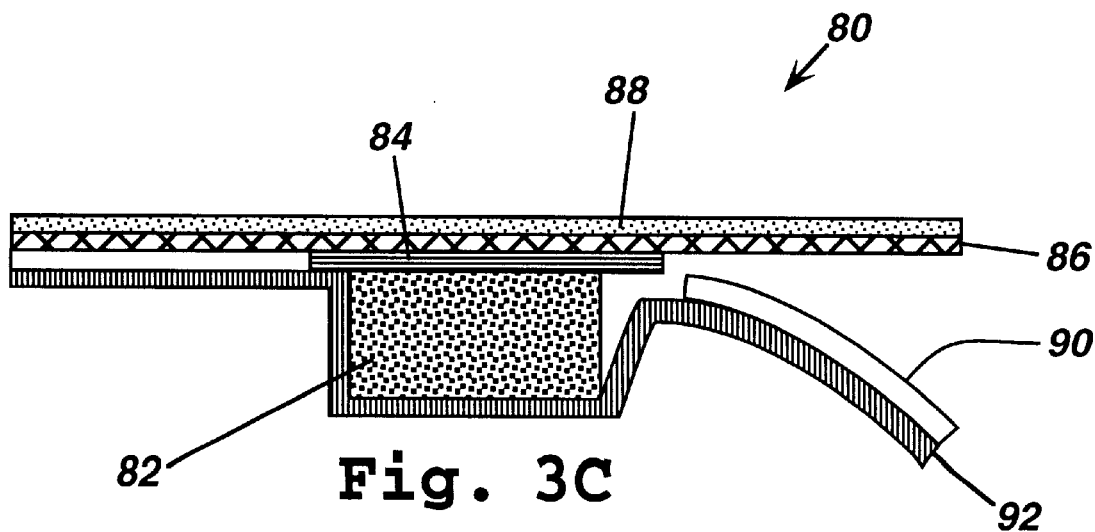

The exemplary transdermal device 40 shown in FIG. 3A includes a reservoir 42 defined by an impermeable backing layer 44 and a membrane 46. The backing layer and the membrane are joined together about the outer periphery of the device, as indicated at 48. These layers are joined by an adhesive, a heat seal or the like. Device 40 also includes an adhesive layer 50 as a means for affixing the device to the skin of a subject. A release liner 52 is removed prior to use of the device to expose adhesive layer 50.

Backing layer 44 defines the distal side of the patch, that is, the side furthest from the skin in use. The backing layer functions as the primary structural element of the device and provides the device with its mechanical properties, e.g., flexibility. The backing layer serves as a protective, impermeable covering to prevent loss of the contents within reservoir 42. Suitable backing materials include commercially available films for medical use, such as those supplied by 3M corporation, Dow Chemical or Fasson Medical Industries. Typical backing materials are made from polyester or the like and may be pigmented or metallized.

Membrane 46 is a highly porous member which retains the formulation within reservoir 42, i.e., it deters bulk flow of the formulation out of the reservoir, but allows passage of the formulation from the reservoir into the skin. Materials suitable for use as membrane 16 include non-woven fabrics such as nonwoven polyesters, polyethylene, polypropylene and other synthetic polymers. The material is preferably heat or otherwise sealable to the backing layer to provide a barrier to transverse flow of reservoir contents.

Reservoir 42, defined by the space or gap between the backing layer and the membrane, provides a storage structure in which to retain the suspension of lipid vesicles to be administered. The lipid vesicle suspension will be described in detail below.

Adhesive layer 50 is the means by which the device is affixed to the skin. This layer is made from a pharmaceutically acceptable pressure sensitive adhesive, such as polydimethylsiloxane, polyisobutylene, polyacrylate, polyurethane and the like. As shown in FIG. 3A, adhesive layer 50 is an in-line adhesive. It will be appreciated that the adhesive layer can also be a peripheral, or rim, adhesive layer, as shown in FIG. 3B.

Device 40 includes a peel strip or release liner to cover the surface of the adhesive layer and to prevent loss of reservoir contents during storage. Prior to use, the release liner is removed from the device. The release liner is typically a material impermeable to the reservoir contents, for example polyethylene terephthalate, and is releasable usually by treatment with a silicone or fluorocarbon.

Referring now to FIG. 3B, a second exemplary transdermal device 60 is shown, comprising a backing layer 62, a membrane 64, and a peripheral adhesive layer 66. In this embodiment, backing layer 62 and membrane 64 are heat sealed about the periphery of the device, as indicated at 68. A reservoir 70 defined by the space between the backing layer and the membrane provides for storage of a suspension of lipid vesicles to be administered transdermally. Peripheral adhesive layer 66 is applied directly to backing layer 62. A release liner 72 protects the device during storage. Materials suitable for the backing layer, the membrane, the adhesive and the release liner are as described for FIG. 3A.

A third exemplary transdermal device 80 is shown in FIG. 3C. In this device, the contents in reservoir 82 are in direct contact with the skin when the device is affixed to a subject. The reservoir in this device is composed of an absorbent sponge or a porous, highly permeable polymer. Materials suitable for the reservoir include polyurethane, polyethylene or polypropylene materials. An impermeable backing layer 84 prevents loss of reservoir contents through the distal, top side of the device. The backing layer is coated on its distal side with an adhesive overlay 86, which is protected by a backing or polymer layer 88. Prior to use, the peripheral edge of the adhesive overlay is exposed by peeling a release liner 90 and an impermeable protective strip 92 from the proximal, skin side of the device.

In the above described embodiments, the devices are adhesively attached to the skin of the user, although other means for attaching the device to the skin are contemplated and suitable, such as an elastic arm band or an adjustable belt.

The membrane in the transdermal device is preferably a porous, highly permeable membrane with, relative to the skin, minimal resistance to diffusion of the reservoir contents. At the same time, the membrane functions to prevent bulk flow the reservoir contents from the device. As will be discussed below, the reservoir includes lipid vesicles in suspension, and the lipid vesicles cross the membrane to contact and penetrate the skin for administration of the entrapped immunogen. Materials suitable for use as a membrane include hydrophilic and hydrophobic fabrics, cloths and polymer films having a porosity suitable for transport of lipid vesicles. Such materials may be nonwoven or may be a woven material having a defined pore size. One preferred material is Pecap™ polyester HC7-51 having a 51 $\mu$m pore size (Tetco, Inc., Briarcliff Manor, N.Y.). Other preferred materials are Saatifil polyester PES47126 (Saati Corp, Stamford, Conn.) and 9-COP-105 Fluortex having a 105 $\mu$m mesh size (Tetco, Inc., Briarcliff Manor, N.Y.).

It will be appreciated that the membrane can be selected to provide more or less diffusional resistance as desired. For example, to design a device where the membrane is rate controlling, rather than the skin, a membrane with a tighter weave or smaller pore size can be selected.

B. Preparation of the Transdermal Device

A biphasic lipid vesicle suspension including the immunogen to be administered transdermally is contained within the reservoir of a transdermal device, such as those illustrated in FIGS. 3A–3C. Preparation of such devices is known to those of skill in the art, and preparation of a specific example of a transdermal device in accordance with the invention is described in Example 2, discussed below.

It will be appreciated that the membrane in the transdermal device is selected depending, in part, on the size of the biphasic lipid vesicles. Typically, the pores of the membrane have a diameter slightly larger than the diameter of the lipid vesicles. In preferred embodiments, the membrane has pores in the size of 0.1–500 $\mu$m, more preferably between 0.1–200 $\mu$m. The size difference between the membrane pore size and the lipid vesicle diameter influences the rate of release of the biphasic lipid vesicles from the device. The smaller this difference is, the slower the rate of lipid vesicle transfer.

In one embodiment of the invention, biphasic lipid vesicles having a heterogeneous size distribution are contained in the reservoir of the device. The smaller vesicles include a first immunogen and/or adjuvant and the larger vesicles contain a second immunogen and/or adjuvant. For a given membrane, the smaller vesicles are released from the device at a faster rate than the larger vesicles, resulting in a first administered and a second administered composition.

V. Method of Use

In another aspect, the invention includes a method for eliciting an immune response to an immunogen in a subject. The method includes administering transdermally to the subject the immunogen entrapped in biphasic lipid vesicles as described herein. In one embodiment, the biphasic lipid vesicles are administered from a transdermal delivery device, such as described above with respect to FIGS. 3A–3C.

In studies performed in support of the present invention, biphasic lipid vesicles were prepared to include leukotoxin, an exotoxin produced by *Pasteurella haemolytica. P. haemolytica* is a gram negative bacteria commonly isolated from the lungs of cattle with pneumonic pasteurellosis (Collier, et al, 1962). Leukotoxin has been identified as a potential virulence factor (Benson, et al., 1978; Berggren, et al., (1981)) and the recombinant protein produced in *E. coli* is used to immunize cattle to protect against fibrinous pneumonia (Harland, et al., 1992). For purposes of the present invention, leukotoxin was used as a model antigen to demonstrate transdermal delivery of a vaccine antigen to elicit an immune response, e.g., an antibody response, in mice.

As described in Example 1, biphasic lipid vesicles were prepared according to the procedure described above to include leukotoxin. A vesicle-forming lipid, hydrogenated phosphatidylcholine, and cholesterol were dissolved in propylene glycol (see Table 1 in the Example for component amounts). An oil-in-water emulsion was prepared by making an aqueous solution containing the antimicrobial agents methylparaben and propylparaben. The lipophilic components were blended together, olive oil, glycerol monostearate, cetyl alcohol, synthetic beeswax, and homogenized with the aqueous phase in the presence of the surfactant Phospholipid EFA to form a surfactant-stabilized oil-in water emulsion.

The emulsion and an aqueous solution of 10 mg/ml leukotoxin were added simultaneously to the lipid components under conditions effective to form biphasic multilamellar lipid vesicles. The preparation was maintained at 40–45° C., mixed with a vortex mixer for 5 minutes. Biphasic lipid vesicles of about 0.5–10 μm were obtained.

Transdermal patches were prepared as described in Example 2. The reservoir of each patch was filled with 60 mg of a suspension of biphasic lipid vesicles, where the lipid vesicles contained either 50 μg or 100 μg of leukotoxin. The patches were affixed to mice, as described in Example 3, and left in place for three days. Three weeks later, the immunization was repeated, by applying a fresh patch to each test mouse and leaving the patch in place for three days. Ten days after the second immunization on day 21, the mice were bled and the serum analyzed for antibodies specific for leukotoxin, as set forth in Example 3.

The results are shown in FIG. 4 where the optical density at 405 nm for a control patch, that is a patch containing placebo biphasic lipid vesicles, and for patches containing either 50 μg or 100 μg leukotoxin entrapped in biphasic lipid vesicles is shown. The results indicate that after immunization with 50 μg or 100 μg leukotoxin transdermally from biphasic lipid vesicles significant antibody levels can be achieved.

FIG. 5 shows the proliferative response of bulk spleen cells isolated from control and leukotoxin immunized mice using the present invention. Bulk spleen cells were isolated from the immunized and control mice and proliferation was measured by incubating the cells in the presence of 25 μg/ml of leukotoxin. The results are expressed as a mean stimulation index of three independent experiments, as set forth in Example 4.

FIG. 6 is a graph showing the secretion of interleukin-4 by bulk spleen cells as measured by a spot enzyme linked immuno-sorbent assay (ELISA). IL-4 secreted by spleen cells isolated from control and leukotoxin-immunized mice was measured. Following the immunization regimen, as described hereinbelow, spleen cells were isolated, exposed to leukotoxin. IL-4 producing cells were identified by counting the number of colonies secreting IL-4, as set forth in Example 5.

In other studies performed in support of the invention biphasic lipid vesicles containing hen egg lysozyme were prepared and delivered transdermally to animals. As described in Example 6, transdermal delivery devices including lipid vesicle-entrapped hen egg lysozyme were prepared. Five different biphasic lipid vesicle formulations were prepared, indicated as numbers I–V. Each of the formulations contained vesicle-forming lipid, hydrogenated phosphatidylcholine, and cholesterol, and differed in the components of the oil-in-water emulsion. Each formulation included 20 mg/ml of hen egg lysozyme.

As described in Example 7, the five different transdermal formulations were tested in vivo by affixing the devices to mice and measuring the immune response elicited. The test animals were immunized twice at a 3 week interval by affixing a new patch for a 3 day dosing period at each of the two immunization time points. Ten days after the second immunization, the mice were euthanized for assessment of the immune response to hen egg lysozyme.

FIG. 7 is a bar graph showing the hen egg lysozyme-specific IgG response in serum of the test animals, measured by optical density at 405 nm as described in Example 7. The data shows that all of the test formulations were effective to elicit an immune response as evidenced by the hen egg lysozyme-specific IgG titres in the serum of the test animals. Mice immunized with lipid vesicle formulation no. V had the highest levels of antigen-specific IgG in serum. The anti-hen egg lysozyme IgG response was characterized primarily by IgG1 subclass for all of the test formulations, as seen in Table 2.

TABLE 2

| | Hen egg lysozyme-specific IgG Isotype (GM)* | | | |
|---|---|---|---|---|
| Formulation | IgG1 | IgG2a | IgG2b | IgG3 |
| Control | <40 | <40 | <40 | <40 |
| I | 402000 | 365 | 445 | 749 |
| II | 77040 | 1352 | 395 | 1681 |
| III | 728900 | 460 | 471 | 5964 |
| IV | 260400 | 490 | 1505 | 454 |
| V | 1335000 | 2036 | 3450 | 4379 |

*Titres are expressed as the geometric mean of 5 individual mice.

FIGS. 8A–8D are plots showing the secretion of interleukin-4 and interferon-γ by bulk spleen cells (FIGS. 8A–8B) and draining lymph node cells (FIGS. 8C–8D) following in vitro topical immunization of 50 μg of hen egg lysozyme from each of the biphasic lipid vesicle formulations nos. I–V. The cells were cultured, as described in Example 8, in the presence of 20 μg/ml of hen egg lysozyme and the frequency of interleukin-4 and interferon-γ secreting cells in the lymph nodes and the spleen was assessed by ELISPOT. As seen, in vitro antigen stimulation of cells from these tissues showed a predominant interleukin-4 response over interferon-γ.

Figure 9:
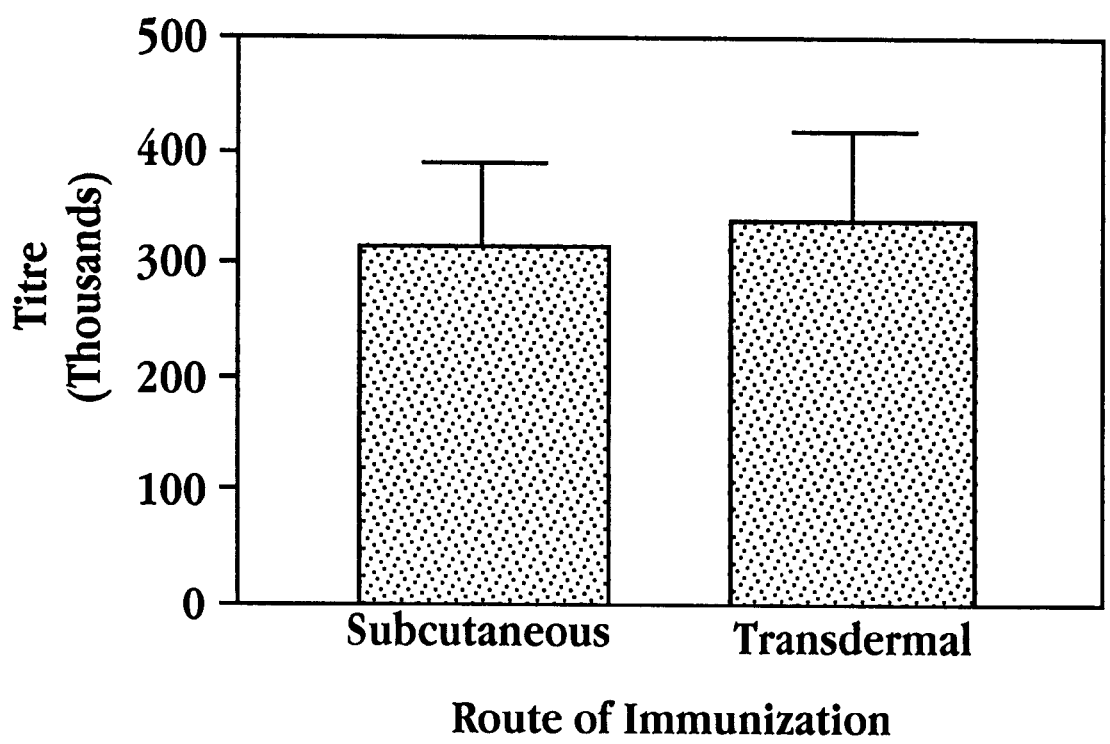
FIG. 9 is a bar graph showing the IgG response in mouse sera following subcutaneous and transdermal immunization with hen egg lysozyme entrapped in biphasic lipid vesicles.

The effect of route of administration was examined by administering 50 μg of hen egg lysozyme entrapped in biphasic lipid vesicles transdermally and subcutaneously. After immunization, the mouse sera was analyzed for levels of anti-hen egg lysozyme using ELISA. As seen in FIG. 9, the hen egg lysozyme-specific antibody response elicited by the transdermal route was comparable to that achieved by subcutaneous administration.

The timing and dose of immunizations can be determined by the skilled artisan based on the known mechanisms of immune activation. Immune responses follow characteristic patterns following immunization with an immunogen. Initially, a lag phase is encountered between the time that a subject is immunized and the logarithmic increase in antibody levels. An initial exposure to the immunogen leads to an increase in antibody levels, primarily IgM antibodies against antigenic epitopes on the immunogen, which tapers off by about week three post immunization. A subsequent immune challenge, three to four weeks after the first exposure, leads to a vigorous immune response, where the primary class of antibody is the IgG class. This secondary immune response is greater in intensity and longer in duration.

Generally, immunization protocols to determine the appropriate response to an antigen fall within parameters known in the art. The dose of a particular immunogen will depend on its antigenic potential, size and diversity of epitopes, as well as the immunogen's ability to stimulate antigen presenting cells. Examples of dose ranges for different classes of immunogens are found below in Table 3.

TABLE 3

| Immunogen | Preliminary Dose | Final Boost Dose |
|---|---|---|
| Soluble and membrane proteins | 10–100 μg | up to 500 μg |
| Nucleic acids | 200 μg | 200 μg |
| Eukaryotic cells | 2–20 × 10$^6$ | 2–20 × 10$^6$ |
| Bacterial cells | 50 μg | 50 μg of protein |
| Viruses | 50 μg 10$^7$ particles (3 doses-weekly) | |
| Fungal antigens | 20–100 μg | 10–100 μg |

In an immunization regimen that includes bacteria or viruses, attenuated forms of the immunogens are used so as to prevent infectious disease. Bacteria and viruses can be attenuated or inactivated by exposing them to, for example, high temperatures, chemical denaturing agents, or by growing them under anaerobic conditions. Chemical modification of immunogens can include formulation, methylation, acylation or crosslinking of the immunogens to themselves, or with other modifying agents.

The immunogen does not have to be in a pure form to be effective. To ensure the best chance of a specific epitope or epitopes, and of a specific type of immune response (humoral versus cellular) the immunogen may be further purified or synthesized. For example, small compounds that are covalently attached to proteins can be used to stimulate humoral responses specific to the epitope of choice. On the other hand, peptides specific for stimulating a particular class of T-cells, such as cytotoxic cells or helper cells via presentation on class I or class II major histocompatibility complex (MHC), respectively, may be pursued, as is known to those in the art of antigen processing and presentation.

IV. Examples

The following examples illustrate preparation and use of the device present invention. The examples are in no way intended to limit the scope of the invention.

Example 1

Preparation of Biphasic Lipid Vesicles Containing Leukotoxin

A. Preparation of Lipid Components

Lipid components, hydrogenated phosphatidylcholine (Phospholipon 90H™, Natterman GmbH, Germany) and cholesterol, were mixed in the amounts shown in Table 1 with propylene glycol and mixed with warming to between about 65–75° C.

B. Preparation of Oil-in-water Emulsion

An oil-in-water emulsion was prepared by mixing the surfactant linoleamidopropyl propylene glycol-dimonium chloride phosphate (Phospholipid EFA™, Mona Industries Inc., Patterson, N.J.), methylparaben and propylparaben, in the amounts shown in Table 1, in distilled water.

In a separate container, the lipophilic components olive oil, glycerol monostearate, cetyl alcohol and synthetic beeswax were blended together.

The water phase and the oil phase were mixed together in a high pressure homogenizer (H-5000 Laboratories Homogenizer Microfluidic Corp.) at 40 psi for 20 minutes. Visually, the emulsion is a milky solution having the consistency of water.

C. Biphasic Lipid Vesicle Formation

The lipid components and the oil-in-water emulsion were mixed together by vortexing or propeller mixing at 50–300 rpm.

TABLE 1

| Component | % (w/w) |
|---|---|
| hydrogenated phosphatidylcholine | 7 |
| Cholesterol | 2 |
| Propylene glycol | 7 |
| 10 mg/mL Leukotoxin in water | 20 |
| Phospholipid EFAJ | 4 |
| Methylparaben | 0.15 |
| Propylparaben | 0.05 |
| Olive oil | 4 |
| Glycerol monostearate | 1 |
| Cetyl alcohol | 0.6 |
| Synthetic Beeswax | 0.28 |
| Distilled water | 53.92 |

Example 2

Preparation of Transdermal Device

A transdermal device was prepared from the following materials as follows.

A backing layer was die cut from Scotchpak™ 1009 (3M Corporation, St Paul, Minn.), a heat sealable polyester film, to a diameter of 18 mm.

An annular ring having an outer diameter of 18 mm and an inner diameter of 10 mm of a pharmaceutical grade transfer adhesive (3M Corporation, #9871) was laminated to the backing layer.

The release liner from the transfer adhesive was removed and a foam ring (ARCare 7298 Medical Foam, Adhesives Research, Inc., Glen Rock, Pa.) with an outer diameter of 18 mm and an inner diameter of 10 mm was secured to the adhesive-coated backing layer. The rim of the ring not in contact with the backing layer was coated with a medical grade adhesive.

The patch was filled with 60 mg of a suspension of biphasic lipid vesicles, where the vesicles contained either 50 μg or 100 μg leukotoxin and were prepared as described in Example 1.

After filling, a membrane of PeCap™ (polyester HC7-51 from 3M Corporation), cut as a disc having an outer diameter of 12 mm, was laminated to the rim of the foam ring.

An 18 mm disc of release liner, 3M Corporation #1022, was laminated to the skin side of the patch.

The devices had an outer diameter of 18 mm, with an active delivery area of 7.8 mm².

Example 3

Transdermal Administration of Leukotoxin from Biphasic Lipid Vesicles

Devices prepared as described in Example 2 were tested on female Balb/c mice, 6–8 weeks of age (Animal Resource Center (University of Saskatchewan)). The mice were anesthetized by halothane (MTC Pharmaceuticals, Cambridge, Ontario) inhalation, and hair was removed from the back area with an electric razor. The patches containing the vaccine formulation were applied to the shaved skin 24 hours after shaving and patches were secured with a plastic bandage. The patch was left in place for 3 days. The immunization was repeated on day 21 and the animals were bled 10 days later and the serum was analyzed for antibody titres specific for leukotoxin as follows.

Antibody titres specific for leukotoxin were determined by ELISA. Ninety-six-well plates (Immulon 2; Dynatech Laboratories, Alexandria, Va.) were coated with purified leukotoxin (0.05 μg/well) in a carbonate/bicarbonate buffer (pH 9.6). The plates were incubated overnight at 4° C. and then washed 4 times in PBS-T containing 0.5% gelatin. Four-fold dilutions of mouse sera were prepared in PBS-T and dispensed in 200 μl volumes. The plates were incubated for 1 hour and washed. Affinity-purified horse anti-mouse IgG (H & L)-biotin conjugate (Vector Laboratories Inc., Toronto, Ontario)) at a dilution of 1/5,000 were used as the detecting antibodies. After incubation for 2 hours and after four subsequent washes, a 1/10,000 dilution of streptavidin-alkaline phosphatase (BIO/CAN) in PBS-T (containing 0.5% gelatin) was added for 1 hour at room temperature. Di(Tris) p-nitrophenyl phosphate (PNPP, Sigma Chemical Co., St. Louis, Mo.) was used as chromogenic substrate. The absorbance was read after 10 minutes at 405 nm (Bio-Rad, Richmond, Calif.).

Figure 4:
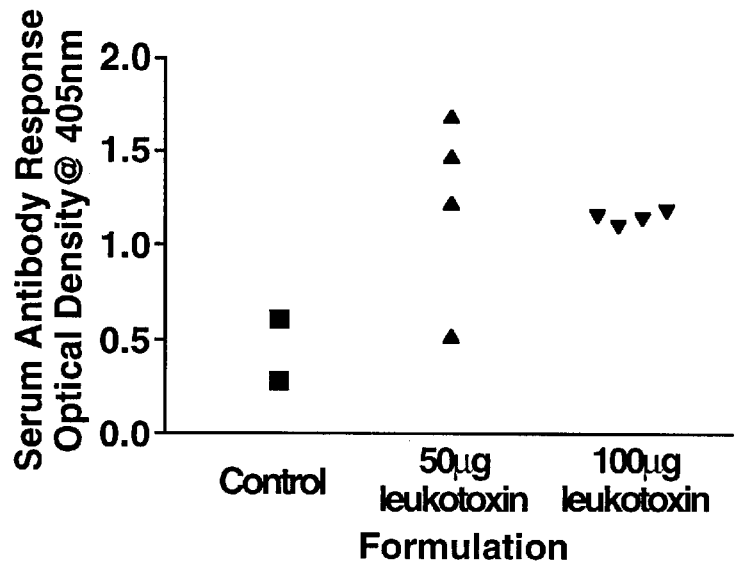
FIG. 4 is a plot showing serum antibody responses, expressed as optical density at 405 nm, following administration of biphasic lipid vesicle-entrapped leukotoxin transdermally from a device in accordance with the invention.

The results are shown in FIG. 4, where the optical density at 405 nm is shown for the animals treated with a control patch (patch reservoir contains placebo biphasic lipid vesicles) and for animals treated with patches containing 50 μg or 100 μg leukotoxin entrapped in biphasic lipid vesicles.

Example 4

Proliferative Responses of Spleen Cells to Leukotoxin

Spleens were aseptically removed from naive and immune mice and teased through a nylon mesh. Most of the red cells were removed in a 1 minute lysis step using TRIS buffered ammonium chloride (0.75%). Nucleated spleen cells were washed twice and subsequently resuspended in culture medium.

Culture medium consisted of AIM-V (Gibco-Life Technologies, Burlington, Canada), supplemented with 100 U/ml of penicillin and 100 μg/ml of streptomycin (Sigma Chemical Co.), 2 mM L-glutamine (Gibco-Life Technologies), 100 μM non-essential amino acids (Gibco-Life Technologies), 1 mM HEPES (Gibco-Life Technologies), and $5 \times 10^{-5}$ M 2-mercaptoethanol (Sigma Chemical Co.).

A. Proliferation

Figure 5:
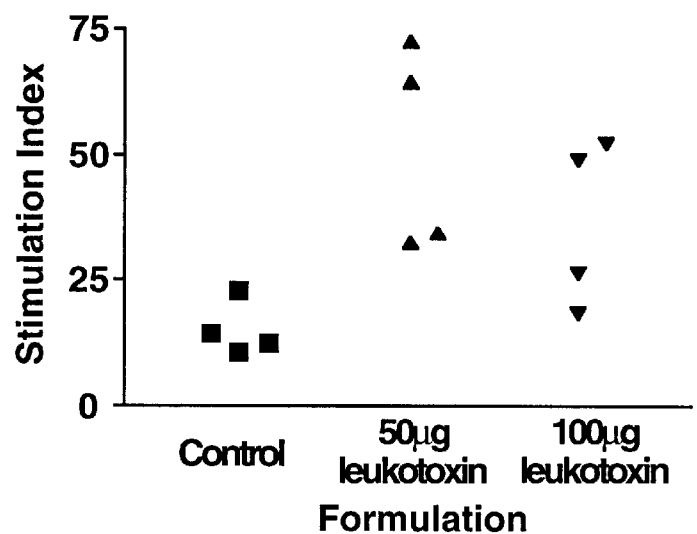
FIG. 5 is a plot showing the proliferative response of bulk spleen cells isolated from control mice (solid squares) and from mice immunized with leukotoxin, administered from transdermal patches containing 50 µg (solid triangles) or 100 µg (inverted triangles) leukotoxin entrapped in biphasic lipid vesicles.

Two×10⁵ spleen cells were dispensed in 100 μl volumes into the wells of microtitre plates. Various concentrations of leukotoxin antigen were added in a 100 μl volume to triplicate wells. After three days in culture the cells were labeled with [³H]thymidine (Amersham, Oakville, Canada) at a concentration of 0.4 μCi/well. The cells were harvested 18 hours later and thymidine incorporation was assessed by scintillation counting. Proliferative responses, expressed as a stimulation index (counts per minute in the presence of antigen/counts per minute in the absence of antigen), are shown in FIG. 5.

Example 5

Quantitation of IL-4 Secreting Spleen Cells

Interleukin-4-specific ELISPOT assay was used as previously described (Czerkinsky, et al., 1988). Briefly, spleen cells were incubated in culture medium at 37° C. and 5% CO₂ for 24–48 hours in the presence or absence of leukotoxin (0.5 μg/ml). The cells were washed twice and resuspended to the appropriate concentration in culture medium. Nitrocellulose plates (Millipore Multiscreen-HA; Millipore, Bedford, Mass.) were coated for 2 hours at ambient temperature with 2 μg/ml of purified anti-mouse interleukin-4 (IL-4) (11B11, Pharmingen, San Diego, Calif.) diluted in 50 mM carbonate/bicarbonate buffer (pH 9.6). Unbound antibody was removed by washing once in phosphate buffered saline (PBS) containing 0.05% Tween 20 (Sigma Chemical Co.) (PBS-T) and three times with PBS. This was followed by a blocking step in culture medium for 2 hours. The medium was decanted and 100 μl of each cell suspension was added to triplicate wells. After an overnight incubation, the plates were washed in cold PBS-T to remove all cells.

Figure 6:
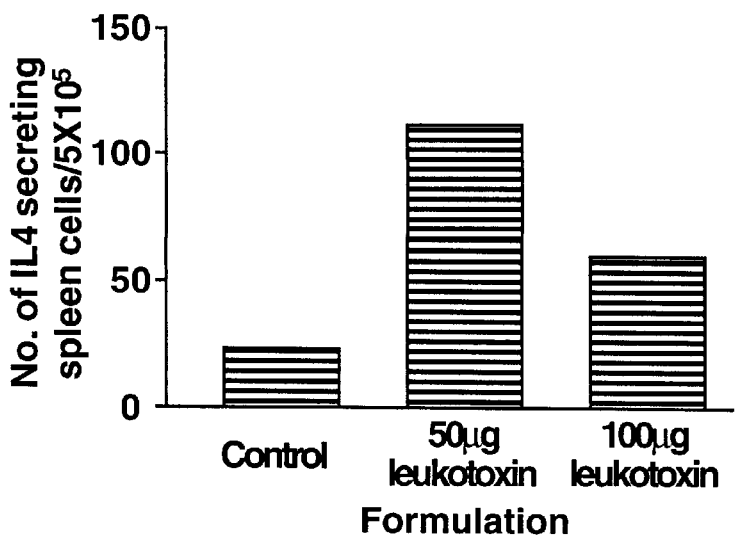
FIG. 6 is a plot showing the secretion of interleukin-4 by bulk spleen cells as measured by a spot enzyme linked immuno-sorbent assay (ELISPOT), for control mice and for mice immunized with leukotoxin, administered at from transdermal patches containing 50 µg or 100 µg leukotoxin entrapped in biphasic lipid vesicles.

The sandwich ELISA for IL-4 was completed using biotinylated antibodies specific to mouse IL-4 (BVD5-24G2, Pharmingen) that was diluted to a concentration of 3 μg/ml in 0.1% BSA/PBS. One hundred microliters of each suspension were added to the respective wells and incubated for 2–4 hours at ambient temperature. The plates were washed three times in PBS-T. A 1/1000 dilution of streptavidin-alkaline phosphatase (BIO/CAN Scientific, Mississauga, Ontario, Canada) in 0.1 BSA/PBS was prepared and dispensed in 100 μg volumes. Incubation was for 2 hours at ambient temperature followed by 8 consecutive washes in PBS. The substrate was prepared as follows: 5-bromo-4-chloro-3-indolyl phosphate (BCIP) (Sigma Chemical Co.) was dissolved in dimethylformamide (Sigma Chemical Co.) to a 14 mg/ml to a 15 mg/ml concentration and 1.5 mg was added to 10 ml of a 15 mM borate buffer (pH 9.8) containing 3 mg of nitro-blue tetrazolium (NBT) (Sigma Chemical Co.). Magnesium chloride was added to a 5 mM concentration. The substrate was filtered and added to the wells in 100 μl volumes and incubated at room temperature for 10–60 minutes. The plates were washed in distilled water and subsequently air dried. Spots representing the location where IL-4 was secreted by spleen cells during the overnight incubation were counted using a dissecting microscope. The results are plotted in FIG. 6, where the values are expressed as the number of positive, stained spots per $5 \times 10^5$ cells.

The results are expressed as the mean standard deviation of spleen cells pooled from four mice, and reflect the activation of interleukin-4 secreting cells. Interleukin-4, also known as B-cell growth factor-1, is a T-cell derived cytokine that triggers the proliferation of antigen-primed B-cells. IL-4 not only stimulates the proliferation of B-cells but enhances the expression of class II-MHC on the surface of antigen presenting cells as well as the activation of T-cell cytotoxic activity.

Example 6

Preparation of Transdermal Devices Containing Hen Egg Lysozyme Entrapped in Biphasic Lipid Vesicles Hen egg lysozyme (Sigma, St. Louis, Mo.) was formulated into biphasic lipid vesicles according to the procedure of Example 1. Five different biphasic lipid vesicle formulations were prepared, identified herein as formulation nos. I–V, each including in the lipid vesicle lipid bilayer hydrogenated phosphatidylcholine (Phospholipon™ 90H) and cholesterol. The formulations differ primarily in the composition of the oil-in-water emulsion. Each formulation includes 20 mg/ml hen egg lysozyme.

Transdermal patches were prepared as described in Example 2 and filled with 60 mg of one of the formulations, to obtain a 100 $\mu$g dose of hen egg lysozyme per patch.

Example 7

Transdermal Administration of Hen Egg Lysozyme

Female Balb/c mice were 6–8 weeks of age and were provided by the Animal Resource Center (University of Saskatchewan). Mice were anesthetized by halothane (MTC Pharmaceuticals, Cambridge, Ontario) inhalation, and shaved on the back by an electric razor. The patches containing different the biphasic lipid vesicle vaccine formulations nos. I–V (Example 6) were applied to the shaved skin, fixed and secured with a plastic bandage. Animals were immunized twice at a 3 week interval and euthanized 10 days after the last immunization to assess immune responses to hen egg lysozyme. For each immunization freshly prepared patches were used and left for 3 days.

Figure 7:
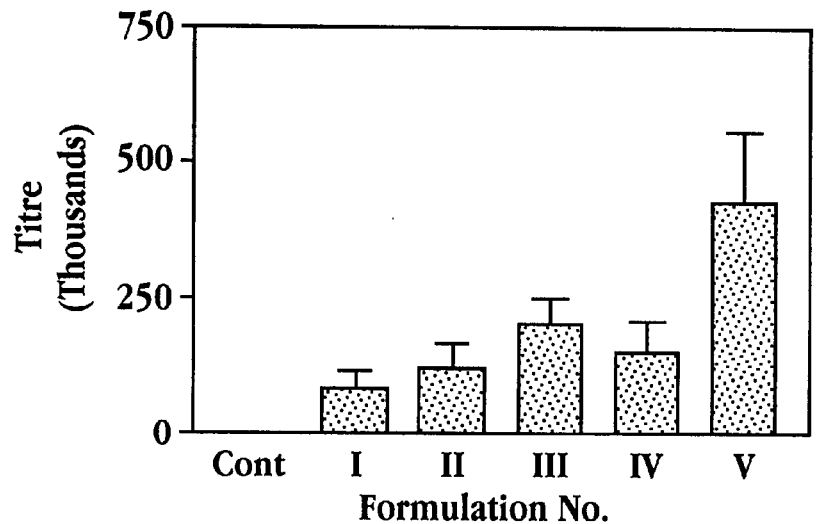
FIG. 7 is a bar graph showing the serum IgG response in mice immunized with transdermally administered hen egg lysozyme with various biphasic lipid vesicle formulations no. I–V.
Figure 8A:
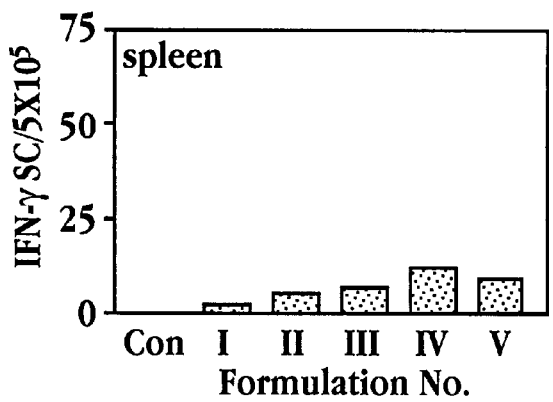
FIGS. 8A–8D are bar graphs showing the secretion of interleukin-4 and interferon-γ from spleen cells (FIGS. 8A–8B) and from draining lymph node cells (FIGS. 8C–8D) following immunization with 50 µg hen egg lysozyme from various biphasic lipid vesicle formulations nos. I–V, as measured by ELISPOT assay.
Figure 8B:
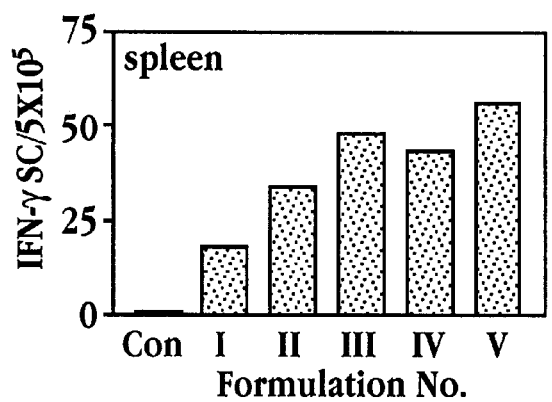
Figure 8C:
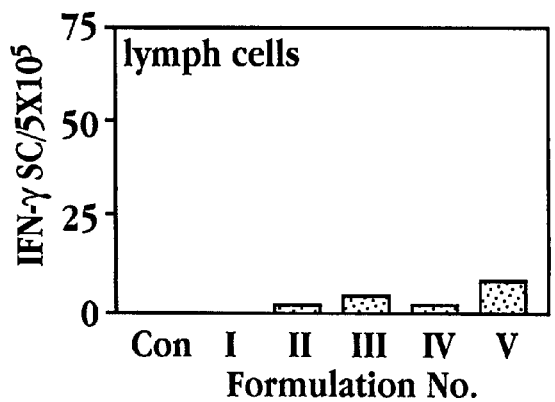
Figure 8D:
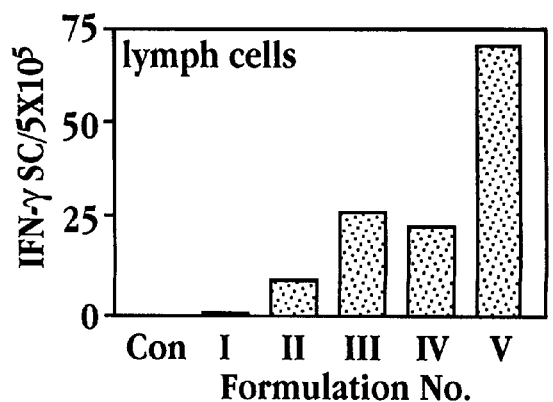

Antibody titres specific for hen egg lysozyme were determined by ELISA. Ninety-six-well plates (Immulon 2; Dynatech Laboratories Inc., Alexandria, Va.) were coated with purified hen egg lysozyme (0.05 $\mu$g/well) in a carbonate/bicarbonate buffer (pH 9.6). The plates were incubated overnight at 4° C. and then washed 4 times in PBS-T containing 0.5% gelatin. Four-fold dilutions of mouse sera were prepared in PBS-T and dispensed in 200 $\mu$l volumes. The plates were incubated for 1 hour and washed. Affinity-purifiedhorse anti-mouse IgG (H & L)-biotin conjugate (Vector Laboratories Inc., Toronto, Ont.) at a dilution of 1/5,000 were used as the detecting antibodies. After incubation for 2 hours and four subsequent washes, a 1/10,000 dilution of streptavidin-alkalinephosphatase (BIO/CAN) in PBS-T (containing 0.5% gelatin) was added for 1 hour at room temperature. Di(Tris) p-nitrophenyl phosphate (PNPP, Sigma) was used as chromogenic substrate. The absorbance was read after 10 minutes at 405 nm (BIO-RAD, Richmond, Calif.). The results are shown in FIG. 7.

Example 8

Quantitation of IL-4 and INF-$\gamma$ Secreting Spleen and Lymph Cells

Spleens were aseptically removed from naive and immune mice and teased through a nylon mesh. Most of the red cells were removed in a 1 minute lysis step using TRIS buffered ammonium chloride (0.75%). The cells were washed twice and subsequently resuspended in culture medium.

Culture medium consisted of AIM-V (Gibco, Life Technologies, Burlington, CanadaLouis,) supplemented with 100 U/ml of penicillin and 100 $\mu$g/ml of streptomycin (Sigma Chemical Co. St Louis, Mo.), 2 mM L-glutamine (Gibco, Life Technologies), 100 $\mu$M non-essential amino acids (Gibco, Life Technologies), 1 mM sodium pyruvate (Gibco, Life Technologies), 10 mM HEPES (Gibco, Life Technologies), and $5 \times 10^{-5}$ M 2-mercaptoethanol (Sigma Chemical Co.).

An ELISPOT assay was used to quantify the frequency of interleukin-4 (IL-4) and interferon-$\gamma$ (IFN-$\gamma$) secreting cells. Briefly, spleen cells were incubated in culture medium at 37° C. and 5% $CO_2$ for 24–48 hours in the presence or absence of hen egg lysozyme (2 $\mu$g/ml). The cells were washed twice and resuspended to the appropriate concentration in culture medium. Nitrocellulose plates (Millipore Multiscreen-HA; Millipore, Bedford, Mass.) were coated for 2 hours at ambient temperature with 2 $\mu$g/ml of purified anti-mouse IL4 (11B11) or anti-mouse IFN-$\gamma$ (R4-6A2) (Pharmingen, San Diego, Calif.) diluted in 50 mM carbonate/bicarbonate buffer (pH 9.6). Unbound antibody was removed by washing once in phosphate buffered saline (PBS) containing 0.05% Tween 20 (Sigma Chemical Co.) (PBS-T) and three times with PBS. This was followed by a blocking step in culture medium for 2 hours. The medium was decanted and 100 $\mu$l of each cell suspension was added to triplicate wells. After an overnight incubation, the plates were washed in cold PBS-T to remove all cells. Biotinylated antibodies specific to mouse IL-4 (BVD6-24G2) or IFN-$\gamma$ (XMG1.2) (Pharmingen) was diluted to a concentration of 3 $\mu$g/ml in 0.1% BSA/PBS. One hundred microliters of each suspension were added to the respective wells and incubated for 2–4 hours at ambient temperature. The plates were washed three times in PBS-T. A 1/1000 dilution of streptavidin-alkaline phosphatase (BIO/CAN Scientific, Mississauga, Ont. Canada) in 0.1% BSA/PBS was prepared and dispensed in 100 $\mu$l volumes. Incubation was for 2 hours at ambient temperature followed by 8 consecutive washes in PBS. The substrate was prepared as follows: 5-bromo-4-chloro-3-indolylphosphate (BCIP) (Sigma Chemical Co.) was dissolved in dimethylformamide (Sigma Chemical Co.) to a 15 mg/ml concentration and 1.5 mg was added to 10 ml of a 15 mM borate buffer (pH 9.8) containing 3 mg of nitro-blue tetrazolium (NBT) (Sigma Chemical Co.). Magnesium chloride was added to a 5 mM concentration. The substrate was filtered and added to the wells in 100 $\mu$l volumes and incubated at room temperature for 10–60 minutes. The plates were washed in distilled water and subsequently air dried. Spots were counted using a dissecting microscope. Values are expressed as the number of positive, stained spots per $5 \times 10^5$ cells and are shown in FIGS. 8A–8D.

Although the invention has been described with respect to particular embodiments, it will be apparent to those skilled in the art that various changes and modifications can be made without departing from the invention.

It is claimed:

1. A composition for transdermal administration of an immunogen, comprising a suspension of biphasic lipid vesicles obtainable by (i) preparing an oil-in-water emulsion, said oil-in-water emulsion stabilized by a surfactant and (ii) mixing said oil-in-water emulsion with vesicle-forming lipids, said lipid vesicles composed of a lipid-bilayer membrane enclosing a central core compartment containing the surfactant-stabilized oil-in-water emulsion, and entrapped in the biphasic lipid vesicles, an immunogen effective to elicit an immune response against the immunogen when the composition is applied to the skin of a subject.

2. The composition of claim 1, wherein the immunogen is selected from the group consisting of antigens derived from bacterial, viral, parasitic, plant and fungal origin.

3. The composition of claim 1, wherein the immunogen is effective to elicit a humoral immune response.

4. The composition of claim 1, wherein the immunogen is effective to elicit a cell-mediated immune response.

5. The composition of claim 1, which further includes an adjuvent entrapped in the lipid vesicles.

6. The composition of claim 1, where the suspension of lipid vesicles further includes a skin permeation enhancer.

7. The composition of claim 6, wherein the permeation enhancer is selected from the group consisting of fatty acylated amino acids and unsaturated fatty acids.

8. A method for eliciting in a subject an immune response to an immunogen, comprising administering transdermally to said subject, a dose of said immunogen, said immunogen entrapped in biphasic lipid vesicles obtainable by (i) preparing an oil-in-water emulsion, said oil-in-water emulsion stabilized by a surfactant and (ii) mixing said oil-in-water emulsion with vesicle-forming lipids, said lipid vesicles composed of a lipid-bilayer membrane enclosing a central core compartment containing the surfactant-stabilized oil-in-water emulsion.

9. The method of claim 8, wherein the immunogen is an antigen of bacterial, viral or fungal origin.

10. The method of claim 8, wherein the immunogen is effective to elicit a humoral immune response.

11. The method of claim 8, wherein the immunogen is effective to elicit a cell-mediated immune response.

12. The method of claim 8, which further includes an adjuvant entrapped in the lipid vesicles.

13. The method of claim 8, wherein said suspension of lipid vesicles is contained in a reservoir adapted for retention thereof.

14. The method of claim 13, wherein said reservoir is defined by an impermeable backing member and a membrane effective in use to allow passage of said lipid vesicles from said reservoir.

15. The method of claim 8, wherein said suspension of lipid vesicles further includes a permeation enhancer.

16. The method of claim 15, wherein said permeation enhancer is selected from the group consisting of fatty acylated amino acids and unsaturated fatty acids.

17. A method for transdermally administering an immunogen to a subject, comprising applying a device to the skin of a subject, said device including
(i) a suspension of lipid vesicles obtainable by (i) preparing an oil-in-water emulsion, said oil-in-water emulsion stabilized by a surfactant and (ii) mixing said oil-in-water emulsion with vesicle-forming lipids, said vesicles composed of (a) a lipid-bilayer outer membrane composed of said vesicle-forming lipids, (b) a central core compartment containing said oil-in-water emulsion and (c) entrapped in said vesicles, a dose of an immunogen effective to elicit an immune response;
(ii) a reservoir adapted to retain said lipid vesicle suspension and adapted for release of lipid vesicles therefrom; and
(iii) means for affixing the device to a subject for transdermal administration of said immunogen.

18. The method of claim 17, wherein said reservoir is defined by an impermeable backing member and a membrane effective in use to allow passage of said lipid vesicles from said reservoir.

19. The method of claim 17, wherein said suspension of lipid vesicles includes a permeation enhancer.

20. The method of claim 19, wherein said permeation enhancer is selected from the group consisting of fatty acylated amino acids and unsaturated fatty acids.

21. The method of claim 17, wherein said means for affixing is an adhesive layer adjacent said membrane.

22. The method of claim 17, which further includes an adjuvant, entrapped in said lipid vesicles.

23. A device for transdermal administration of an immunogen, comprising a suspension of lipid vesicles obtainable by (i) preparing an oil-in-water emulsion, said oil-in-water emulsion stabilized by a surfactant and (ii) mixing said oil-in-water emulsion with vesicle-forming lipids, said vesicles composed of (i) a lipid-bilayer outer membrane composed of such vesicle-forming lipids, (ii) a central core compartment containing such an oil-in-water emulsion and (iii) entrapped in said vesicles, a dose of an immunogen effective to elicit an immune response;

a reservoir adapted to retain said suspension and adapted for release of lipid vesicles therefrom; and means for affixing the device to a subject for transdermal administration of said immunogen.

24. The device of claim 23, wherein said reservoir is defined by an impermeable backing member and a membrane effective in use to allow passage of said lipid vesicles from said reservoir.

25. The device of claim 23, wherein said suspension of lipid vesicles includes a permeation enhancer.

26. The device of claim 23, wherein said permeation enhancer is selected from the group consisting of fatty acylated amino acids and unsaturated fatty acids.

27. The device of claim 23, wherein said means for affixing is an adhesive layer adjacent said membrane.

28. The device of claim 23, which further includes an adjuvant, entrapped in said lipid vesicles.

* * * * *